United States Patent [19]

Osberghaus et al.

[11] 3,933,923

[45] Jan. 20, 1976

[54] PROCESS FOR THE MANUFACTURE OF VICINAL GLYCOLS

[75] Inventors: Rainer Osberghaus, Dusseldorf-Urdenbach; Werner Stein, Erkrath-Unterbach, both of Germany

[73] Assignee: Henkel & Cie GmbH, Dusseldorf-Holthausen, Germany

[22] Filed: Nov. 7, 1973

[21] Appl. No.: 413,690

[30] Foreign Application Priority Data
Nov. 20, 1972 Germany............................ 2256907

[52] U.S. Cl.......... 260/615 R; 260/633; 260/635 E; 260/637 R
[51] Int. Cl.².................. C07C 29/00; C07C 41/02
[58] Field of Search............. 260/635 E, 633, 615 R

[56] References Cited
UNITED STATES PATENTS

| | | | |
|---|---|---|---|
| 2,650,940 | 9/1953 | Young | 260/635 E |
| 2,694,077 | 11/1954 | Stansbury et al. | 260/635 E |
| 2,934,505 | 4/1960 | Gurgiolo | 260/615 B |
| 2,983,763 | 5/1961 | Krause | 260/615 B |
| 3,020,293 | 2/1962 | Schonberg et al. | 260/635 E |

*Primary Examiner*—Joseph E. Evans
*Attorney, Agent, or Firm*—Hammond & Littell

[57] ABSTRACT

A process for the manufacture of higher vicinal diols or polyols by hydrolysis of the corresponding mono- or poly-epoxides, characterized in that the hydrolysis is carried out using aqueous solutions of salts of aliphatic mono- and/or polycarboxylic acids and temperatures above 100°C, preferably 200° to 350°C, and if necessary, in the presence of dissolving intermediaries.

9 Claims, No Drawings

PROCESS FOR THE MANUFACTURE OF VICINAL GLYCOLS

THE PRIOR ART

It is known that lower-molecular weight water-soluble epoxides, for example, ethylene oxide, can be hydrolyzed to the corresponding diols when they are subjected to acid-catalyzed saponification under normal pressure at moderate temperatures or when they are subjected to neutral hydrolysis in water at high temperatures and high pressure. Both processes are not suitable for the hydrolysis of higher molecular weight water-insoluble epoxides, because these processes produce mediocre yields of the diol or because large quantities of side reaction by-products are produced or because lengthy reaction times are required even when the reaction conditions are modified. In addition, hydrolysis with sodium hydroxide at temperatures of about 200°C has been described as specially suitable for the hydrolysis of branched epoxides. The maximum yields obtained by the use of this process are 76%. It is also known that higher linear epoxides do not give any higher yield when this process is used.

According to J. Am. Chem. Soc. 66, 1925 (1944), another possibility for the conversion of long-chain epoxides to diols consists in that first the epoxides are converted to hydroxyacetoxy compounds by heating with glacial acetic acid and then the esters thusly formed are saponified with alkalis. As a rule, such a two-step procedure is too expensive for a technical process.

OBJECTS OF THE INVENTION

It is an object of the present invention to provide a process for the manufacture of higher vicinal diols or polyols by hydrolysis of the corresponding mono- or poly-epoxides, characterized in that the hydrolysis is carried out using aqueous solutions of salts of aliphatic mono- and/or polycarboxylic acids and temperatures above 100°C, preferably 200° to 350°C, and if necessary, in the presence of dissolving intermediaries.

This and further objects of the invention will become apparent as the description thereof proceeds.

DESCRIPTION OF THE INVENTION

The present invention concerns a process for the manufacture of vicinal glycols by the hydrolysis of alkylene oxides.

The advance in the art according to the present invention is that before now no process was known, according to which epoxides could be converted to vicinal glycols by the use of a single-step process resulting in yields of over 90%.

Concerning the manufacture of higher vicinal diols and polyols by the hydrolysis of the corresponding epoxides, it has now been discovered that the above-described drawbacks of the prior art can be obviated by the use of a process which is characterized by carrying out the hydrolysis of the epoxides by using aqueous solutions of salts of aliphatic mono- and/or polycarboxylic acids at temperatures above 100°C and, if necessary, in the presence of dissolving intermediaries.

The temperature range of 200° to 350°C is preferred.

More particularly, the present invention provides a development in the process for the preparation of higher vicinal diols and/or higher vicinal polyols which comprises hydrolyzing the corresponding epoxides of the formula

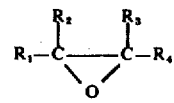

in which $R_1$, $R_2$, $R_3$ and $R_4$ are each selected from the group consisting of hydrogen, alkyl having 1 to 28 carbon atoms, haloalkyl having 1 to 28 carbon atoms, alkoxyalkyl having 2 to 28 carbon atoms, epoxyalkyl having 3 to 28 carbon atoms, haloepoxyalkyl having 3 to 28 carbon atoms, alkoxyepoxyalkyl having from 4 to 28 carbon atoms, and mixtures thereof, with the proviso that the total number of carbon atoms in the epoxide is from 4 to 30 carbon atoms, with a solution of a catalyst, and recovering said diols and/or polyols; wherein the improvement comprises carrying out said hydrolysis with a catalyst comprising an aqueous solution of salts of an aliphatic carboxylic acid having 1 to 24 carbon atoms selected from the group consisting of a monocarboxylic acid having 1 to 24 carbon atoms, a polycarboxylic acid having 3 to 24 carbon atoms and mixtures of a monocarboxylic acid having 1 to 24 carbon atoms with a polycarboxylic acid having 3 to 24 carbon atoms, at a temperature above 100°C, optionally in the presence of dissolving intermediaries, said carboxylic acid salts being stable under the reaction conditions and being soluble in the form of their salts.

Suitable salts for carrying out the process of the invention are the salts of carboxylic acids which are stable under the reaction conditions and are soluble in the form of their salts. The respective aliphatic monocarboxylic acids or polycarboxylic acids can be saturated or unsaturated, linear or branched compounds, and if so desired, can also be heterosubstituted compounds which can be used individually or as a mixture. When monocarboxylic acid salts are used exclusively, then consideration as to sufficient solubility restricts the main choice to compounds having up to 10 carbon atoms, if a dissolving intermediary is not utilized. However, if a dissolving intermediary is utilized in the amount of at least 0.5 parts by weight per part by weight of epoxide to be hydrolyzed, then only monocarboxylic acid salts of acids having more than 10 carbon atoms up to 24 carbon atoms may be utilized in lower concentrations of from 1% to 5% by weight, preferably from 2% to 4% by weight, of the aqueous solution. Preferred are the monocarboxylic acid salts of acids having 8 to 22 carbon atoms such as alkanoic acids having 12 to 16 carbon atoms, such as lauric acid, myristic acid and palmitic acid.

Examples of suitable salts of carboxylic acids are preferably the monosalts and polysalts of alkali metals, such as the lithium salt, dilithium salt, sodium salt, disodium salt, potassium salt, and dipotassium salt, and preferably the monosalts and polysalts of alkaline earth metals such as the calcium salt, dicalcium salt, barium salt and dibarium salt. The respective sodium salts are especially preferred.

Examples of suitable carboxylic acids whose above-named salts can be utilized according to the present invention include linear or branched aliphatic monocarboxylic acids having 1 to 24 carbon atoms, preferably 1 to 10 carbon atoms, for example, alkanoic acids having 1 to 24 carbon atoms, preferably 1 to 10 carbon atoms, such as acetic acid, propionic acid, butyric acid, capronic acid, caprylic acid, pelargonic acid, lauric acid, myristic acid, palmitic acid, stearic acid, and arachic acid, and, for example, alkenoic acids having 3 to 24 carbon atoms, preferably 3 to 10 carbon atoms, such as acrylic acid, methacrylic acid and allylacetic acid, lauroleic acid, myristoleic acid, palmitoleic acid, oleic acid, gadoleic acid and erucic acid. Other suitable examples include linear or branched aliphatic polycarboxylic acids having 3 to 24 carbon atoms, preferably 3 to 10 carbon atoms, for example, alkanedioic acids having 3 to 24 carbon atoms, preferably 3 to 10 carbon atoms, such as malonic acid, succinic acid, adipic acid, azelaic acid and sebacic acid, and, for example, alkenedioic acids having 4 to 24 carbon atoms, preferably 4 to 10 carbon atoms, such as maleic acid and fumaric acid.

The salts of dicarboxylic acids having 3 to 24 carbon atoms are preferred and can be used either by themselves or mixed with monocarboxylic acids. In such mixtures, salts of monocarboxylic acids having more than 10 carbon atoms, for example, up to 24 carbon atoms can likewise be present.

More particularly the salts of aliphatic carboxylic acids having 1 to 24 carbon atoms which may be utilized are salts of carboxylic acids selected from the group consisting of an alkanoic acid having 1 to 24 carbon atoms, an alkenoic acid having 3 to 24 carbon atoms, an alkanedioic acid having 3 to 24 carbon atoms, an alkenedioic acid having 4 to 24 carbon atoms, and a mixture of at least one monocarboxylic acid selected from the group consisting of an alkanoic acid having 1 to 24 carbon atoms and an alkenoic acid having 3 to 24 carbon atoms with at least one dicarboxylic acid selected from the group consisting of an alkanedioic acid having 3 to 24 carbon atoms and an alkenedioic acid having 4 to 24 carbon atoms.

For hydrolysis, the salts of the carboxylic acids are used as aqueous solutions containing 1% to 20% of said salts, preferably as 2% to 5% of said salts.

It is assumed that the epoxide ring is split by hydroxyl ions which arise from the hydrolytic splitting in aqueous solution of the hydrolyzing salts. It is to be regarded as completely surprising that there is no reaction of the oxirane ring with the anions of the carboxylic acid salts nor is there any homopolymerization of the epoxide taking place.

The hydrolysis is preferably carried out in the presence of solution aids, such as dissolving intermediaries, suitable examples of which are all water-soluble alkanones and water-soluble cyclic hydrocarbon ethers, for example, acetone, dioxane, and dioxolane. The quantities of dissolving intermediaries to be used are at least 0.5 parts by weight per part by weight of epoxide to be hydrolyzed. Especially preferred is the proportion of 2 parts by weight of dissolving intermediary to 1 part by weight of the epoxide. The proportion of the salt solution to the epoxide to be hydrolyzed should be at least 0.5 parts by weight of salt solution per part by weight of epoxide. In general, it is preferred to use 2 to 5 parts by weight of salt solution per part by weight of epoxide.

Epoxides having the following formula are to be utilized in the process of the invention:

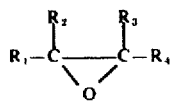

in which $R_1$, $R_2$, $R_3$ and $R_4$ are each selected from the group consisting of hydrogen, alkyl having 1 to 28 carbon atoms, preferably having 1 to 16 carbon atoms, haloalkyl having 1 to 28 carbon atoms, preferably having 1 to 16 carbon atoms, alkoxyalkyl having 2 to 28 carbon atoms, preferably having 2 to 16 carbon atoms, epoxyalkyl having 3 to 28 carbon atoms, preferably having 3 to 16 carbon atoms, haloepoxyalkyl having 3 to 28 carbon atoms, preferably having 3 to 16 carbon atoms, alkoxyepoxyalkyl having 4 to 28 carbon atoms, preferably having 4 to 16 carbon atoms, and mixtures thereof, with the proviso that the total number of carbon atoms in the epoxide is from 4 to 30 carbon atoms.

In the substituents $R_1$, $R_2$, $R_3$ and $R_4$ the epoxides can contain branched chains and hetero atoms or hetero atom groups which do not participate in the reactions for the preparation of the epoxides nor in the hydrolysis reaction, for example, halogen atoms or ether groups. Suitable examples of the epoxides to be hydrolyzed according to the process of the invention include: epoxyalkanes having 4 to 30 carbon atoms, preferably 4 to 20 carbon atoms, for example, 1,2-epoxybutane, 2,3-epoxybutane, 1,2-epoxyhexane, 1,2-epoxyoctane, 3,4-epoxyoctane, 1,2-epoxydodecane, 1,2-epoxyhexadecane, 1,2-epoxyoctadecane, 1,2-epoxyheptadecane; and diepoxyalkanes having 4 to 30 carbon atoms, preferably 8 to 20 carbon atoms, such as 1,2,7,8-diepoxyoctane, as well as mixtures of epoxides which can be prepared by the known epoxidation of olefin fractions having a statistical distribution of the double bond and having 4 to 30 carbon atoms, preferably 15 to 18 carbon atoms.

The reaction can be carried out in such a manner that the mixture of epoxide, salt solution and, if necessary, dissolving intermediary is stirred in the autoclave and heated to the respective reaction temperature whereby especially in the case of 1,2-epoxides, additional heating is for the most part not required, and immediate cooling can be applied. In case that internal epoxides are to be converted, such as, for example, the epoxidation products of olefin fractions, this conversion required somewhat longer reaction times at the above-quoted reaction temperatures.

It is easy to work up the hot reaction mixture by phase separation, if necessary, after any optionally present solvent or dissolving intermediary has been distilled off.

The advantages of the present invention include, in general, that yields obtained by using the process of the invention exceed 90%, and especially when 1,2-epoxides are converted, yields of 100% are readily attainable. As a rule, the conversion of the epoxide utilized amounts to 100%.

The following examples are merely illustrative of the present invention without being deemed limitative in any manner thereof.

EXAMPLES

The Examples summarized in the following Table are based on experiments which were carried out as follows:

The mixture of epoxide and aqueous solution of the carboxylic salt and sometimes acetone as reported in the Table was introduced into a nickel autoclave equipped with a stirrer and was heated to the reported reaction temperature under an inert nitrogen atmosphere at a pressure of 10 atm. gauge. In the case of 1,2-epoxides, the mixture was cooled immediately after the reported reaction temperature had been reached.

The stated yields were determined as follows:

The reaction products were quantitatively extracted with cold or hot chloroform, depending upon their respective solubility, the solvent was distilled off, and the residue was analyzed. The conversion was measured by determination of the residual epoxide content in the reaction product, and the yield of vicinal glycols was determined by titration with periodic acid.

For a check of the results, the diols were distilled or recrystallized and then analyzed again. This second determination was more necessary in the case where there was non-converted epoxide present in the reaction product, because in that case the determination of the diol content could be faulty.

TABLE

| Example No. | Reaction Mixture | Conditions T(°C)/t (min.)** | Conversion % | Yield % Theor. |
|---|---|---|---|---|
| 1 | 1,2-Epoxydodecane (200 gm), 2% aqueous solution of Disodium Azelate (600 gm) | 260/15 | 100 | 90 |
| 2 | 1,2-Epoxydodecane (100 gm), 2% aqueous solu. of Disodium Azelate (300 gm), Acetone (200 ml) | 250/A* | 100 | 99 |
| 3 | 1,2-Epoxyoctane (100 gm), 2% aqueous solu. of Disodium Adipate (300 gm), Acetone (200 ml) | 250/A* | 100 | 97 |
| 4 | 1,2-Epoxyhexadecane (100 gm), 2% aqueous solu. of Sodium Pelargonate (300 gm), Acetone (200 ml) | 250/A* | 100 | 100 |
| 5 | 1,2-Epoxyoctadecane (100 gm), 2% aqueous solu. of Disodium Sebacate (300 gm), Acetone (200 ml) | 250/A* | 100 | 97 |
| 6 | $C_{15}$ to $C_{18}$ Epoxide Mixture with statistically distributed oxirane ring (100 gm), 2% aqueous solu. of Disodium Adipate (300 gm), Acetone (200 ml) | 250/120 | 99 | 93 |
| 7 | $C_{15}$ to $C_{18}$ Mixture of 1,2-Epoxides (100 gm), 2% aq. solu. of Disodium Azelate (300 gm), Acetone (200 ml) | 250/A* | 100 | 97 |
| 8 | 1,2-Epoxyheptadecane (100 gm), 2% aq. solu. of Sodium Laurate (300 gm), Acetone (200 ml) | 250/A* | 100 | 96 |
| 9 | 1,2,7,8-Diepoxyoctane (100 gm), 2% aq. solu. of Disodium Azelate (300 gm), Acetone (200 ml) | 250/A* | 100 | 100 |

*A=After heating to the reaction temperature, cooling was applied immediately.
**t=Reaction time after the stated temperature had been reached.

The vicinal diol reaction products produced according to the process of the present invention may be utilized as intermediates for further reaction processes to produce aldehydes as disclosed in copending U.S. patent application Ser. No. 150,222, filed June 4, 1971, or to produce carboxylic acids as disclosed in copending U.S. patent application Ser. No. 166,309, filed July 26, 1971, now U.S. Pat. No. 3,865,856.

Further advantages attainable by the process of the invention especially include the fact that long-chain epoxides can be hydrolyzed to the corresponding vicinal diols using a one-step process and that high yields can be obtained which hitherto have not been possible to achieve.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. In the process for the preparation of higher vicinal diols and/or higher vicinal polyols comprising hydrolyzing the corresponding epoxides of the formula

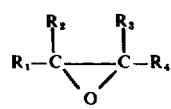

in which $R_1$, $R_2$, $R_3$ and $R_4$ are each selected from the group consisting of hydrogen, alkyl having 1 to 28 carbon atoms, haloalkyl having 1 to 28 carbon atoms, alkoxyalkyl having 2 to 28 carbon atoms, epoxyalkyl having 3 to 28 carbon atoms, haloepoxyalkyl having 3 to 28 carbon atoms, alkoxyepoxyalkyl having from 4 to 28 carbon atoms, and mixtures thereof, with the proviso that the total number of carbon atoms in the epoxide is from 4 to 30 carbon atoms, with an aqueous solution of a catalyst, and recovering said diols and/or polyols; the improvement which comprises carrying out said hydrolysis with a catalyst consisting of an aqueous solution of salts selected from the group consisting of alkali metal salts, alkaline earth salts and mixtures thereof, of carboxylic acids selected from the group consisting of (a) alkanoic acids having from 8 to 22 carbon atoms with at least 0.5 parts by weight per part by weight of said epoxides of dissolving intermediaries, (b) alkanedioic acids having 3 to 24 carbon atoms, (c) alkenedioic acid having 4 to 24 carbon atoms, and (d) a mixture of at least one monocarboxylic acid selected from the group consisting of an alkanoic acid having 1 to 24 carbon atoms and an alkenoic acid having 3 to 24 carbon atoms with at least one dicarboxylic acid selected from the group consisting of an alkanedioic acid having 3 to 24 carbon atoms and an alkenedioic acid having 4 to 24 carbon atoms, at a temperature above 100°C, optionally in the presence of further dissolving intermediaries, said aqueous solution of said salts containing 1% to 20% of said salts and being present in an amount of at least 0.5 parts by weight of said salt solution per part by weight of said epoxide, said dissolving intermediaries being selected from the group consisting of water-soluble alkanones and water-soluble cyclic hydrocarbon ethers,.

2. The process of claim 1, in which said salts of carboxylic acids are salts of alkanoic acids having from 8 to 22 carbon atoms with at least 0.5 parts by weight per part by weight of said epoxide of said dissolving intermediaries.

3. The process of claim 1, in which said temperature ranges between 200° to 350°C.

4. The process of claim 1, in which said salts of carboxylic acids are salts of alkanedioic acids having 3 to 24 carbon atoms.

5. The process of claim 1, in which said salts of carboxylic acids are mixtures of at least one monocarboxylic acid selected from the group consisting of an alkanoic acid having 1 to 24 carbon atoms and an alkenoic acid having 3 to 24 carbon atoms with at least one dicarboxylic acid selected from the group consisting of an alkanedioic acid having 3 to 24 carbon atoms and an alkenedioic acid having 4 to 24 carbon atoms.

6. The process of claim 1, in which the concentration of the salt solutions used for the hydrolysis ranges from 2% to 5%.

7. The process of claim 1, in which the salts to be used for the hydrolysis are the sodium salts.

8. The process of claim 1, in which the amount of dissolving intermediaries used is from 0.5 to 2 parts by weight per part by weight of epoxide.

9. The process of claim 1, in which the dissolving intermediaries used are selected from the group consisting of acetone, dioxane, dioxolane and the mixtures thereof.

* * * * *